United States Patent
Willms et al.

(10) Patent No.: US 6,309,745 B1
(45) Date of Patent: *Oct. 30, 2001

(54) ADHESIVE TAPE AND METHOD FOR PRODUCING IT

(75) Inventors: Eric Joachim Willms; Edgar Lionel Tilly, both of Bad Soden (DE)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,313
(22) PCT Filed: Jun. 7, 1996
(86) PCT No.: PCT/US96/09711
§ 371 Date: Apr. 7, 1998
§ 102(e) Date: Apr. 7, 1998
(87) PCT Pub. No.: WO96/41604
PCT Pub. Date: Dec. 27, 1996

(30) Foreign Application Priority Data

Jun. 13, 1995 (EP) .................................................. 19521879

(51) Int. Cl.[7] .............................. C09J 7/02; A61F 13/58; A61F 13/60; B05D 5/10
(52) U.S. Cl. ....................... 428/354; 428/352; 428/42.1; 428/42.3
(58) Field of Search ...................................... 428/354, 352, 428/42.1, 42.3

(56) References Cited

U.S. PATENT DOCUMENTS

| | | |
|---|---|---|
| 4,054,697 | 10/1977 | Reed et al. ............................... 428/40 |
| 4,067,337 | 1/1978 | Ness ..................................... 128/287 |
| 4,287,255 | 9/1981 | Wong et al. ........................... 428/343 |
| 4,460,634 | 7/1984 | Hasegawa ............................. 428/124 |
| 4,889,234 | 12/1989 | Sorensen et al. ..................... 206/459 |
| 5,288,546 * | 2/1994 | Roessler et al. ...................... 428/284 |
| 5,306,376 * | 4/1994 | James .................................... 428/343 |
| 5,336,541 | 8/1994 | Kobayashi ............................. 428/40 |

* cited by examiner

*Primary Examiner*—Daniel Zirker
(74) *Attorney, Agent, or Firm*—Peter D. Meyer

(57) ABSTRACT

The invention relates to a method for producing an adhesive tape for redetachable closure or fixing, comprising a strip-like carrier (1), which is being coated with a self-adhesive agent (2), at least on the active area which during use of the adhesive tape is brought into contact with a counter surface (7), and also relates to the adhesive tape as such. For improving production of the adhesive tape, several methods are suggested, according to one of which in a first step the active area is coated with a self-adhesive agent (2) forming a continuous layer, and in a second step, in order to reduce the effective entire adhesive area, a non-adhering or less-adhering separating pattern (4) is printed on the self-adhesive layer.

6 Claims, 3 Drawing Sheets

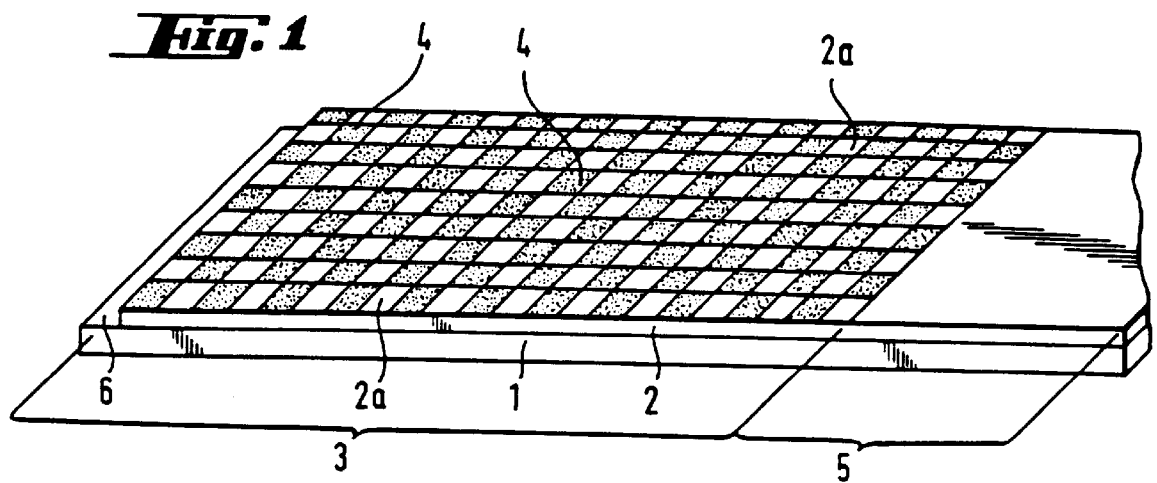
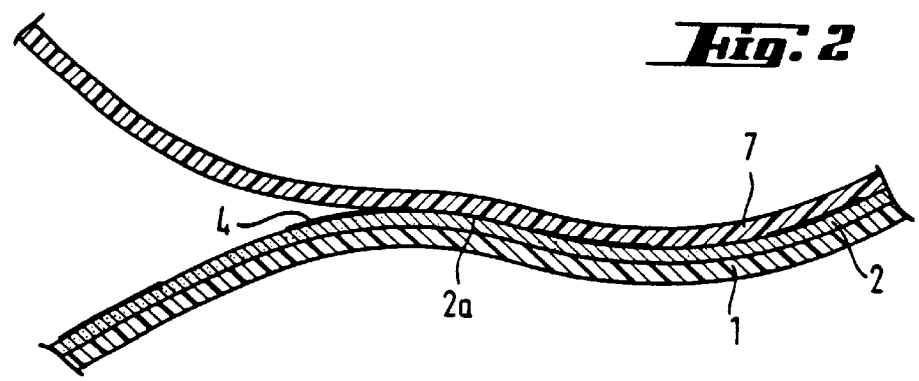
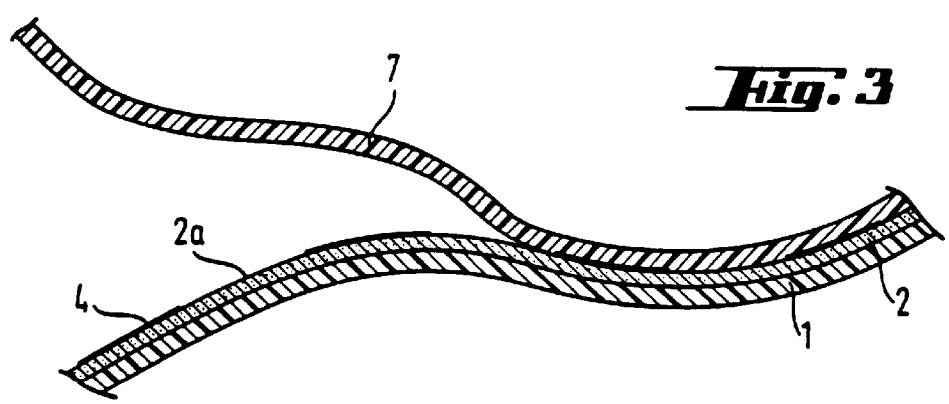

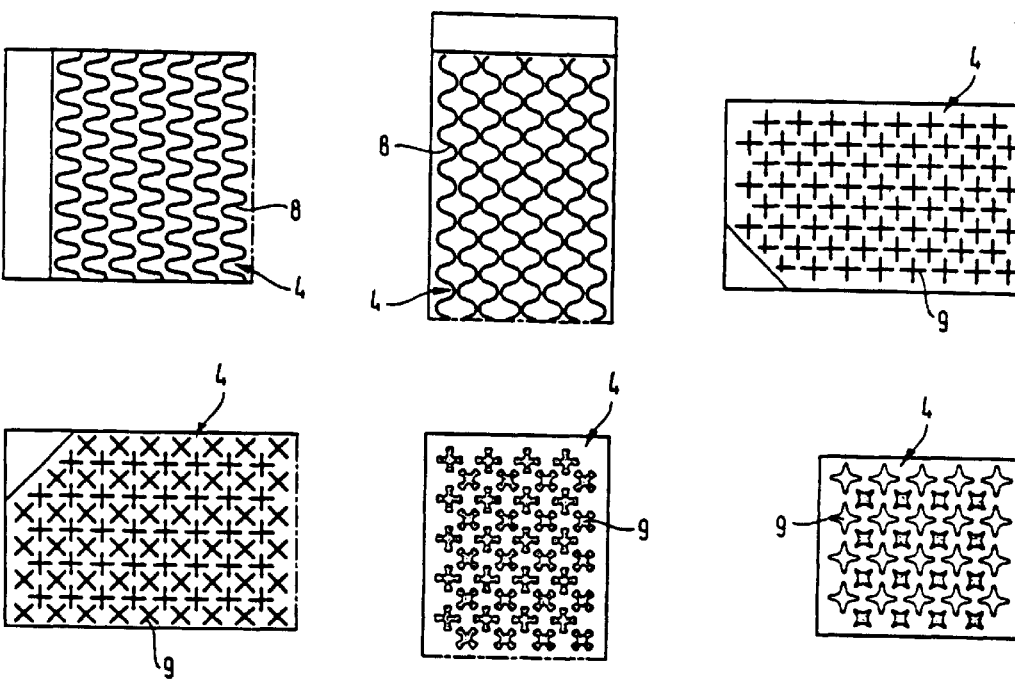
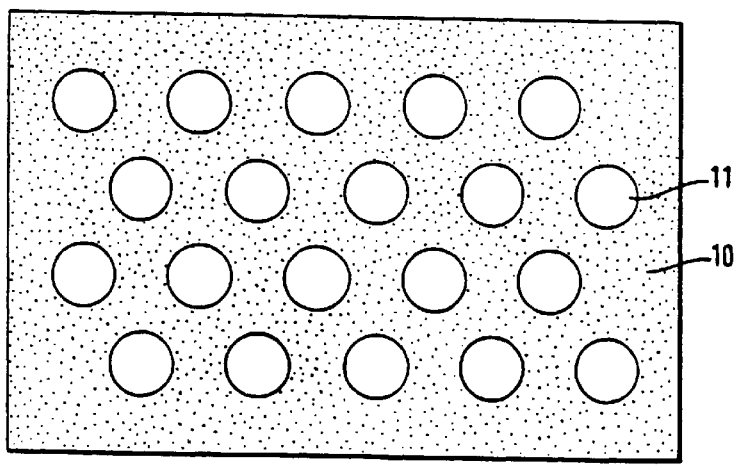
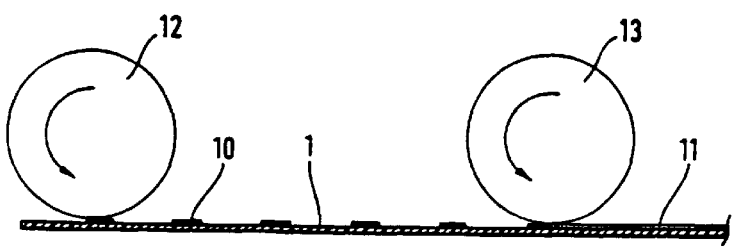

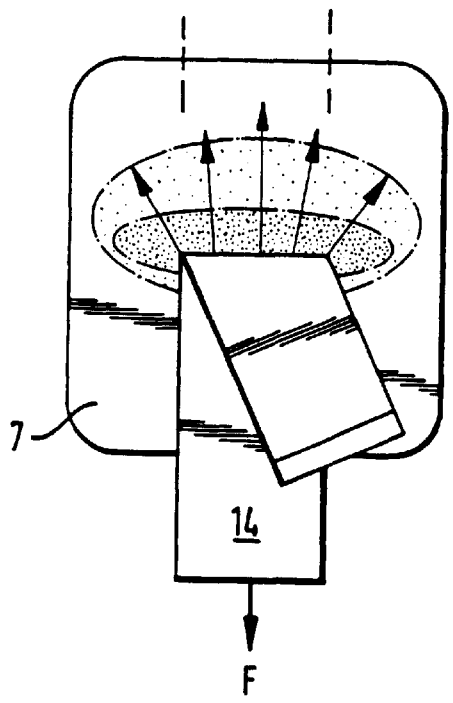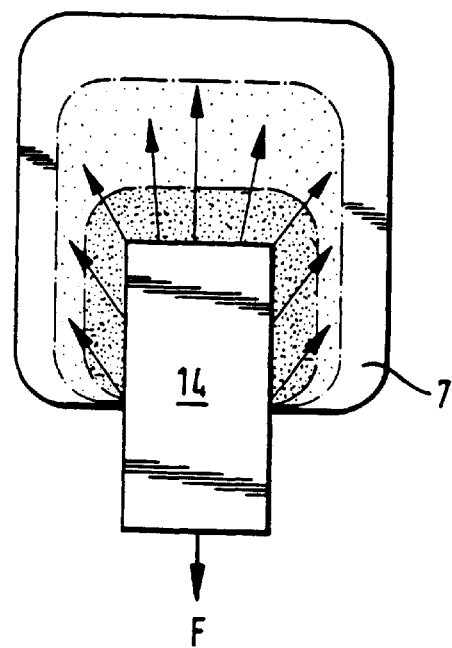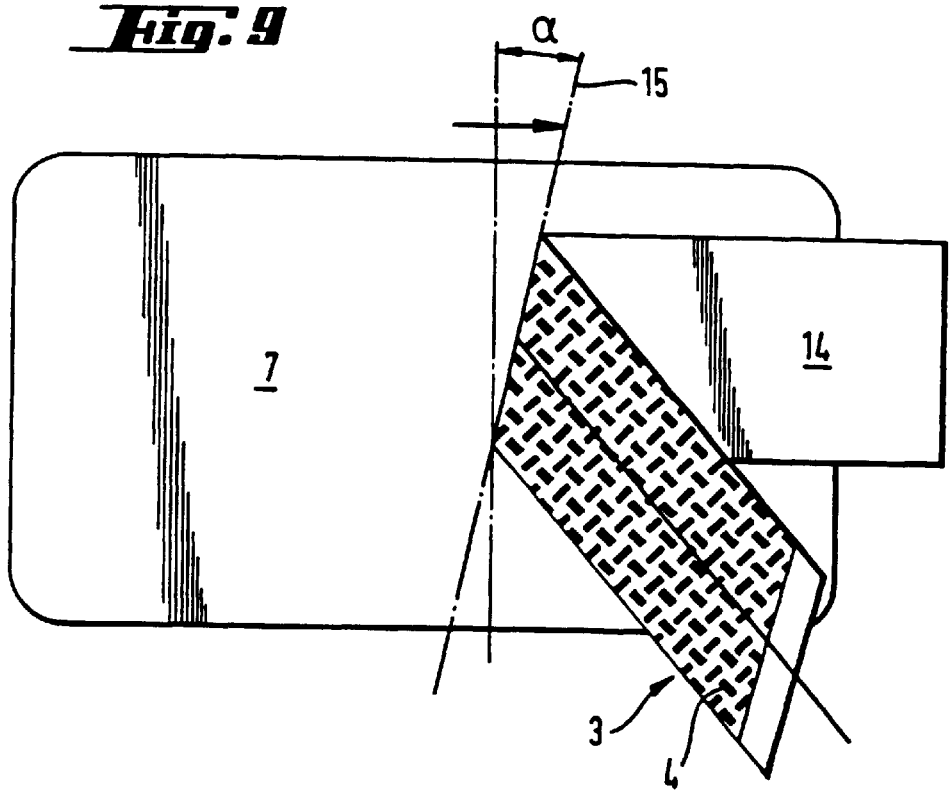

ADHESIVE TAPE AND METHOD FOR PRODUCING IT

The invention relates to a method for producing an adhesive tape for redetachable closure or fixing, comprising a strip-like carrier, said carrier being coated with a self-adhesive agent, at least on the active area which during use of said adhesive tape is brought into contact with a counter surface.

Also, the invention relates to an adhesive tape for redetachable closure or fixing, comprising a strip-like carrier, said carrier being coated with self-adhesive agent, at least on the active area which during use is brought into contact with a counter surface.

In many applications such adhesive tapes should solve two opposing objects: They should have sufficient high adhesion which is ensured already by light pressing of the adhesive tape against an uneven surface, and it should be possible to repeatedly peel them of from said surface for opening without destroying said counter surface. The last mentioned object is particuly difficult to solve if the counter surface against which the adhesive tape is pressed with its redetachable area consists of a thin plastic foil, a sensitive fabric or the like. This problem arises particularly with disposable diapers which are covered on the after donning the diaper outer side with a water proof plastic foil which for cost reasons alone but also for improving wearing comfort should be made as thin as possibly. An adhesive tab used for such a disposable diaper must repeatedly be opened for inspection of the diaper and for correction of the diaper fit. The high adhesive force welcome to ensure a save diaper closure, however, easily causes destruction of said thin cover foil of the diaper when peeling off the adhesive tape.

An extensive discussion of these problems can be found for example in Canadian patent 1 239 752. Suggestions for solving these problems can be found e.g. in EP 0 269 713 E1, EP 0 321 234 B1, U.S. Pat. No. 4,067,337, U.S. Pat. No. 4,210,144 or PCT-application PCT/US92/08950 (WO 93/07845). EP 0 269 713 B1 discloses particularly in FIG. 6 an adhesive tape designed for closing containers, which in its detachable area is provided with an adhesive pattern consisting merely of thin lines.

The section of the adhesive tape designed to be fixed to the counter surface as firm and undetachable as possible comprises on its surface a completely covering, i.e. continuous layer of adhesive agent, while the opposing end of said adhesive tape is free of glue thereby forming a strap which can be grasped by a person in order to lift the section covered with a light adhesive pattern only from the counter surface.

DE 4 202 704 C2 also seems to be pertinent. Disclosed is a fixing tab for a diaper with a flat carrier being coated on one side with discrete adhesive segments made of self-adhesive agent, at least on the section being designed to be sticked during use to the second diaper part, whereby said self-adhesive agent has such adhesive forces that the fixing tab formed by coating with the self-adhesive agent comprises a peel resistance of a defined value against the outer foil of the diaper and can be detached several times from the outer foil and reattached without damaging the foil.

The adhesive tape described in the first paragraph of this specification is disclosed in U.S. Pat. No. 4,067,337. Referring to the embodiments disclosed therein, reduction of the effective adhesive area is accomplished with a grid- or sieve-like super-imposed layer that is placed like a stencil on the continuous layer of adhesive agent, the effective area thereof being reduced to the openings in the stencil. As described in U.S. Pat. No. 3,666,609, particularly a plastic net can be used.

Production of the aforesaid adhesive tape is comparatively complicated and therefore expensive. It is therefore an object of the invention to develop an adhesive tape that can be produced at lower costs, which shows adhesive forces sufficient high also in case the adhesive tape is pressed only slightly against an uneven counter surface, and which, however, can be peeled off several times of a sensitive counter surface, particularly a thin plastic foil, without damaging the latter.

As far as the method is concerned this object is solved by means of the features of claim 1 or, however, with the features of claim 2, and as far as design of the adhesive tape is concerned this object is solved by means of the features of claim 3 or, alternatively, by means of the features of claim 4.

The adhesive tape produced in the inventive manner shows a very good adhesiveness, however, can be lifted easily from the counter surface. During lifting the imprinted separating pattern hinders building up of high forces applied to the counter surface, so that in the course of repeated lifting of the adhesive tape no damage of the counter surface could be observed, e.g. of a counter surface consisting of the thin plastic foil. The surface pattern, e.g. checkered pattern, of the adhesive tape, consisting of adhesive squares or areas and imprinted, non-adhesive areas, will be slightly stretched when lifting off the adhesive tape; the surface of the counter part, e.g. a thin plastic foil, during the lifting procedure is only stretched between two non-adhesive points of the pattern in the peeling direction, whereby the forces imposed on the counter surface are spread evenly in all directions and therefore stress the, e.g. thin foil forming the counter surface only within its elastacy, i.e. without damaging it.

The separating pattern can be comprised of discrete points or areas and/or extended areas. In this context such a geometry of a separating pattern has advantages in which the adhesive layer is interrupted by sections of the separating pattern in the area of the preferred peel line. The preferred peel line can extend exactly transversally to the adhesive tape, it is preferably arranged, however, under a peel angle of e.g. 30.

The separating pattern can be produced using roller printing or by means of a silk screen and is preferably made from paint, ink, powder or silicon oil.

The carrier can be made of foil, paper, woven or non-woven fabric, in case of a foil the foil preferably consists of polyethylene, polypropylene, polyvinylchloride or polyester. Also a fleece or non-woven fabric made of polypropylene or polyester can be used.

The adhesive tape can comprise a second section, adjacent to the active area, which second section comprises a continuous layer of an adhesive agent which is overall active, too. Such a second longitudinal section serves as a means to fix the adhesive tape permanently to a basic surface. The continuous layer of adhesive agent can be the same as the adhesive layer of the first longitudinal section; taking into account special restrictions, however, it can be different.

Furthermore, the carrier can comprise a lift strap arranged in a section adjacent to its active area. The section forming the lift strap can consist of an area free of adhesive agent or of a section that was coated with adhesive agent and covered with a protective foil or separating foil thereafter.

According to an alternative embodiment the active area of the adhesive agent can comprise a continuous layer of adhesive agent which in turn comprises a print coverage thereon covering said first layer completely in order to adjust a reduced adhesive retention force, said print coverage made of a material like paint, ink, powder, silicon oil or the like. By suitable selection of different parameters like the agent or material forming the reducing layer, the thickness of the reducing layer and its moisture content, the aggressive adhesive retention force of the adhesive layer can be reduced to a favourable value.

To enhance conceivable applications of the inventive adhesive tape it can be useful to have the carrier coated with an adhesive layer also on its lower surface. The adhesive layer on the lower surface can be an ordinary, overall active layer of adhesive agent or glue, or can be a special adhesive layer comprising the features of claim 3 or claim 4.

The drawing shows several embodiments of the invention as an example. In the drawings show:

FIG. 1 an adhesive tape in perspective view;

FIG. 2 a section of the adhesive tape shown in FIG. 1 in enlarged scale compared to FIG. 1 at the beginning of lifting off the tape from a foil forming the counter surface;

FIG. 3 the advanced lifting procedure in a depiction according to FIG. 2;

FIG. 4 six different separating patterns;

FIG. 5 in top view an alternative embodiment of an adhesive tape;

FIG. 6 in a schematic drawing production of an adhesive tape according to FIG. 5;

FIG. 7 a symbolic depiction of the peeling forces induced into a counter surface by said adhesive tape;

FIG. 8 the shear forces generated between adhesive tape and counter surface according to FIG. 7 and FIG. 9 the peel angle as well as the peel line.

The adhesive tape shown in FIG. 1 consists of a strip-like carrier 1, being coated on its top surface with a continuous layer of adhesive agent 2. In a first longitudinal section 3 a separating pattern 4 is imprinted on this adhesive layer 2 in order to reduce the active adhesive area, whereby said separating pattern comprises discrete non-adhesive areas which are symmetric and evenly arranged.

In a second longitudinal section 5 adjacent to said separating pattern 4 the adhesive layer 2 is not coated; the active adhesive area is therefore formed by the surface of the second longitudinal section 5, which is used for permanently fixing the adhesive tape to a basic surface.

FIG. 1 furthermore shows that carrier 1 comprises a glue-free section forming a finger lift strap 6 being arranged opposite said second longitudinal section 5.

FIGS. 2 and 3 show a detail of longitudinal section 3 coated with said separating pattern 4 stickingly fixed to a counter surface 7 in form of a plastic foil. Upon lifting the active area of the adhesive tape formed by the first longitudinal section 3 from said plastic foil 7, the uncovered adhesive areas 2a between the imprinted separating areas cause stretching of the related areas of plastic foil 7 each only for a short period of time, so that damage of plastic foil 7 is avoided. Upon separation of adhesive area 2a from plastic foil 7, the areas of plastic foil 7 being stressed by adhesive areas of the adhesive tape can relieve.

FIG. 4 shows six different embodiments for separating pattern 4. Two of these examples show separating pattern 4 comprising extended areas 8, while the remaining four examples comprise discrete areas 9 in form of crosses or asterisks.

FIG. 5 shows an embodiment of the adhesive tape being modified compared to FIG. 1. The first longitudinal section 3 forming the active area of the adhesive tape comprises an imprinted non- or less-adhering separating pattern 10 and an adhesive pattern 11 of self-adhesive agent printed into the blank spaces of said separating pattern. The separating pattern 10 is grid- or sieve-like, while the adhesive pattern 11 is comprised of discrete glue segments. FIG. 6 shows in a symbolic manner production of the active area 3: The carrier 1 is firstly conveyed in direction of the arrow through a printing station 12 for the separating pattern, which imprints separating pattern 10 on the active area 3, and is thereafter conveyed to printing station 13 for the adhesive pattern, printing the adhesive agent in the blank spaces (sieve spaces) of separating pattern 10. In principle, such a printing procedure can be carried out in reversed order, too.

FIG. 7 symbolizes the peel force induced by adhesive tape 14 into counter surface 7, which force between the two dotted lines amounts to about a third of lifting force F and outside this central region amounts to about a sixth of lifting force F.

FIG. 8 symbolizes the shear force between adhesive tape 14 and counter surface 7.

FIG. 9 shows an adhesive tape 14, which is lifted of a counter surface 7 along an advancing peel line 15, which encloses a peel angle a with a line extending transversally of lifting tab 14. According to the invention the separating pattern 4 or 10, respectively, should be arranged or designed in a manner so that peel line 15 consistently crosses sections of separating pattern 4 or 10, respectively, so that in the region of peel line 15 no continuously extending area of adhesive agent or glue exists.

What is claimed is:

1. An adhesive tape comprising:

a carrier, said carrier being coated with a self-adhesive agent, at least on an active area of said carrier which during use is brought into contact with a counter surface wherein said active area consists of a non-adhering or less adhering separating pattern and an adhesive pattern of self-adhesive agent printed into blank spaces of said separating pattern;

said carrier comprising a finger lift strap adjacent to said active area; and, a second section of said carrier longitudinally adjacent to said active area, said second section comprising a continuous adhesive layer, said adhesive layer being active.

2. An adhesive tape as claimed in claim 1 wherein said carrier is a carrier strip.

3. A method for producing an adhesive tape according to claim 1 for redetachable closure or fixing comprising:

providing a carrier;

coating said carrier with a self-adhesive agent at least on an active area of said carrier by forming a continuous layer of said self-adhesive agent;

coating said carrier with a non-adhering or less adhering separating pattern in order to reduce the effective adhesive area on said carrier; and, providing a finger lift strap arranged in a section adjacent to said active area.

4. The method of claim 3 further comprising:

printing said separating pattern on said active area; and, printing said adhesive agent in blank spaces of said non-adhering or less adhering separating pattern.

5. The method of claim 3 further comprising:

activating said non adhering or less adhering substance by optical, physical or chemical means.

6. The method of claim 3 wherein said carrier is a carrier strip.

* * * * *